United States Patent [19]

Palomo Coll

[11] 3,947,465

[45] Mar. 30, 1976

[54] 3-ALKYLSILYL-2-OXAZOLIDINONE COMPOUNDS AND SYNTHESIS THEREOF

[76] Inventor: Antonio Luis Palomo Coll, Maestro Pérez Cabrero 7, Barcelona, Spain

[22] Filed: Feb. 19, 1974

[21] Appl. No.: 443,849

[30] Foreign Application Priority Data

Feb. 21, 1973 Spain .................................. 411867

[52] U.S. Cl. ........ 260/307 C; 260/239.1; 260/243 C
[51] Int. Cl.² ...................................... C07D 263/38
[58] Field of Search ............................... 260/307 C

[56] References Cited
OTHER PUBLICATIONS

Noll–*Chemistry and Technology of Silicones*–Academic Press, New York, (1968), p. 80.

*Primary Examiner*—Raymond V. Rush
*Attorney, Agent, or Firm*—Haseltine, Lake & Water

[57] ABSTRACT

Silylating agents, such as 3-alkylsilyl-2-oxazolidinones, are useful for the preparation of penicillins and cephalosporins at low temperatures and in a short time. The process for preparing these compounds comprises reacting 2-oxazolidinone or 5-methyl-2-oxazolidinone with trimethylchlorosilane, dimethylchlorosilane or triethylchlorosilane, in the presence of an organic tertiary base acting as a hydrogen chloride removal agent.

5 Claims, No Drawings

3-ALKYLSILYL-2-OXAZOLIDONONE COMPOUNDS AND SYNTHESIS THEREOF

FIELD OF THE INVENTION

The present invention relates to a group of compounds of the following general formula:

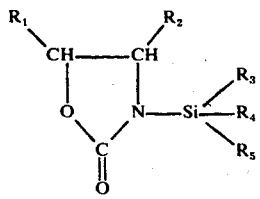

where $R_1$ and $R_2$ are hydrogen, lower alkyls or aryls and $R_3$, $R_4$ and $R_5$ are lower alkyls or one of them is chlorine; and in particular 3-trimethylsilyl-2-oxazolidinone and other similar compounds to a process for preparing them, and to a process for preparing penicillins or cephalosporins using such compounds.

These compounds are particularly valuable in the production of 6(acylamido)penicillanic, 7(acylamido) cephalosporanic and 7(acylamido) desacetoxycephalosporanic acids, which are of interest in view of their value as therapeutic agents in medicine, as supplements in animal feeds and as industrial intermediates.

DESCRIPTION OF PRIOR ART

The use of certain specific silylating agents are reactants for the preparation of penicillins and cephalosporins have been described in the literature. These include hexamethyldisilazan, by Birkofer (Chem. Abstr. 59, 2826, 1963), and N-trimethylsilyldiethylamine, by Rühlman. The main disadvantage of these agents lies in the relatively high temperatures to which the 6-APA is subjected, which is necessary to remove the basic compounds which are formed during the reaction, such as ammonia and dialkylamines, which react intensely with acylating agents. This circumstance also obliges the isolation of the silyl ester of 6-APA. The fact that temperatures of up to 150°C are necessary also imposes a limitation with respect to the use of solvents in the silylation reaction. Accordingly, an excess of the silylating agent is employed as the reaction medium followed by dissolution in a suitable solvent. The trialkylchlorosilane reactants have disadvantage similar to the N,N' alkylsilyldiphenylureas, in that they produce precipitates which are deposited on the silyl ester, thus reducing the active reaction which extends the reaction times. With respect to the quality and purity of the solutions, the hydrochloride of the tertiary base resulting from the action of the chlorosilane on 6-APA in the presence of, for example, triethylamine, gives rise to coloured compounds, according to the operating temperature and time. 7-aminocephalosporanic acid (7-ACA) and particularly 7-aminodesacetoxycephalosporanic acid (7-ADCA), which is practically insoluble in all the usual organic solvents in the presence of an excess of organic bases when in a state of high purity, also react in a similar manner with these silylating agents.

SUMMARY OF THE INVENTION

The abovementioned difficulties and disadvantages have been overcome by the use of the 3-alkylsilyl-2-oxazolidinones now discovered which enable the preparation, under moderate conditions, of silyl esters of 6-APA, 7-ACA and 7-ADCA in a large variety of organic solvents, both protides and aprotides, and of low dielectric constant.

The process for preparing the silylating agents represented by the foregoing general formula consists of reacting a 2-oxazolidinone with a trimethylchlorosilane in the presence of tertiary organic bases. The general method representing the process is defined in the particular case of 3-trimethylsilyl-2-oxazolidinone, which compound is represented by the initials TMSO, whilst the trimethylsilyl group is represented by TMS.

TMSO is produced through the reaction of 2-oxazolidinone (a), trimethylchlorosilane (b) or dimethyldichlorosilane in the presence of tertiary bases such as triethylamine, n-ethylpiperidine, quinoline and picolines as typical examples, which fix the acid forming the corresponding hydrochlorides, in accordance with the following reaction diagram:

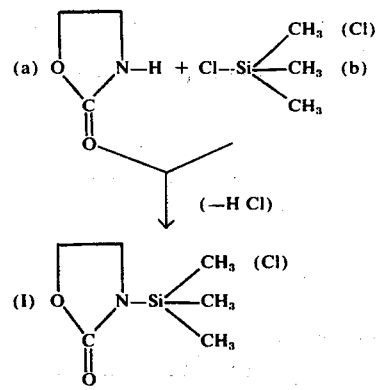

performed in a suitable medium, constituted by an organic solvent preferably characterized by the lower solubility of the hydrochloride of the tertiary base and in which the components (a) and (b) and the silyl derivative (I) are readily soluble. In the preparation of these new silylating agents there are used cheap, widely produced raw materials such as trimethylchlorosilane and dimethyldichlorosilane, 2-oxazolidinone which may be conveniently obtained from monoethanolamine and urea and, likewise the tertiary amines which are readily recoverable from the hydrochlories and reused in the process.

The reaction between oxazolidinone and a halotrialkylsilane, for example, trimethylchlorosilane, is performed under moderate conditions from room temperature to 40°C, low temperatures being preferred in the case of dimethyldichlorosilane, the halogen being removed with a tertiary base. For this purpose, a solution of 2-oxazolidinone and trimethylchlorosilane is prepared, for example, in 1,2-dichlorethane and minimum quantities of triethylamine are added, defined by the stoichiometry of the reaction. The hydrochloride of the tertiary base precipitates almost immediately and is removed by filtration.

Both 3-trimethylsilyl-2-oxazolidinone (TMSO) and 3-chlorodimethylsilyl-2-oxazolidinone (CMSO) have turned out to be excellent agents for the production of silyl esters of 6-APA, 7-ACA and 7-ADCA, the reaction of formation of esters, by basic catalysis, proceeding in accordance with the following diagram:

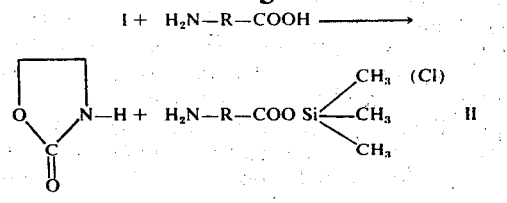

where R is the penam, cepham or cephem structural fraction to designate the bicyclic skeleton present in penicillins and cephalosporins according to the trivial nomenclature indicated by Bose and Manas (Synthesis of Penicillin Cephalosporin C and Analogues; Marcel Dekker, Inc., New York, 1969, p.2).

An important advantage which characterizes these new silylating agents in comparison with the known ones is the release in the reaction medium of a compound, 2-oxazolidinone which, unlike the usual agents, not only does not interfere, since it remains in solution without affecting the balance, but also has been proved to proceed favorably in the acylation process of II to obtain III, improving the quality and yield of conversion in IV by later treatment with water:

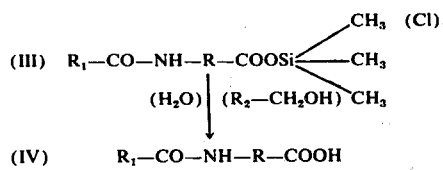

(IV)   $R_1$—CO—NH—R—COOH

The use of these silylating agents is characterized by the release of a 2-oxazolidinone in the reaction medium, which product is also released if the agent is treated with water. This circumstance enables these agents to be easily characterised. The advantage of this intermediate, for example 2-oxazolidinone when using TMSO is its easy conversion into active intermediate, the 3-acyl-2-oxazolidinones, when they are used as acylating agents, the acid anhydrides, acid chlorides or other active forms of the carboxyl group, the reaction proceeding in accordance with the following simplified diagram:

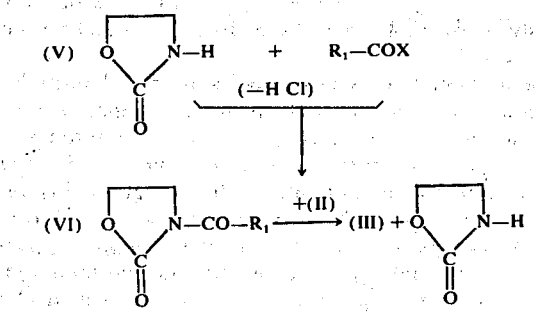

where (V) is 2-oxazolidinone and (VI) is intermediate 3-acyl-2-oxazolidinone and X is a carboxylic acid activator group. The removal of the hydrogen chloride released to form (VI) is performed by the tertiary organic bases or, in their absence, by agents having a regulating effect, such as triethylamine pivalate, normally used in the processes of preparation of penicillins and cephalosporins. The presence of these intermediates is described in some examples to show the particular advantages of the 2-oxazolidinone released by these new silylating agents which potentiate the process of preparation of the above mentioned antibiotics.

The particularly advantageous action of these silylating agents, for example TMSO, is shown in the capacity to form silyl esters in the presence of catalytic amounts of a tertiary base. Thus, when using 7-ADCA in methylene chloride and with heating to reflux (approximately 40°C) a result is obtained in 30 minutes, whilst its equivalent with hexamethyldisilazan is produced in 24 to 48 hours. TMSO with 6-APA in methylene chloride gives rise to the formation of the ester in 5 minutes at the above temperature.

Under the above conditions, these new silylating agents do not cause the epimerization of penicillins and cephalosporins either. This is a very important fact since the epimers of these antibiotics described in the literature have no biological activity and thus cause a low yield of biologically active product. This happens with N,N-bis-(trimethylsilyl)acetamide, as has been shown by Gutowski (Tetrahedron Letters, 1779; 1970) and vanderhaeghe et al. (Tetrahedron Letters, 285, 1972). Epimerization and secondary decomposition reactions are also produced when tertiary organic bases are used to activate the reaction by effect of heat and when the silylating agent is trimethylchlorosilane, hexamethyldisilazan or trimethylsilyldiethylamine.

The advantages offered by TMSO and is special behavior enable the results obtained with this silylating agent to be considered as surprising.

DETAILED DESCRIPTION OF THE INVENTION

EXAMPLE 1. 3-trimethylsilyl-2-oxazolidinone (TMSO)

Triethylamine (60 ml; 0.42 mol) is added to a solution of 2-oxazolidinone (30.5 g; 0.35 mol) in methyl ethyl ketone (500 ml). The solution is chilled with stirring an ice-water bath. Over a period of 15 minutes trimethylchlorosilane (60 ml; 0.44 mol) is poured in gradually whilst the temperature is controlled to between 35° and 40°C. The reaction proceeds without cooling but with stirring and the temperature is allowed to drop. After 45 minutes the reaction liquid is filtered to separate the triethylamine hydrochloride which is washed with a further amount of methyl ethyl ketone. The liquors are brought together, the solvent is evaporated at low pressure with heating in a hot water bath (40°C) to give a more or less light brown fluid oil which is mixed with n-heptane (50 ml) and filtered to remove the triethylamine hydrochloride residue. The yield in crude product is virtually quantitative.

The lower organic phase is decanted, first distilled at a moderately low pressure, the n-heptane is dissolved ($\approx$25%) and thereafter the vacuum is intensified. This gives a colorless liquid corresponding to TMSO (52.2 g; Yield = 93.7%), with density = 1.040 (20°) and boiling point = 97° (3.5 mm).

Alcoholysis with methanol in methylene chloride, with evaporation of the solvent, gives 1.593 g of TMSO and 0.871 g of 2-oxazolidinone. 2-oxazolidinone calculated: 54.67%; found: 54.6%.

EXAMPLE 2. 3-triethylsilyl-2-oxazolidinone (TMSO)

Following the previous example, but replacing the trimethylchlorosilane with triethylchlorosilane (63.3 g; 0.42 mol) and operating under similar conditions, the result is the compound of the above heading; a colorless fluid liquid, obtained with a similar yield. 2-oxazolidinone, calculated: 42.82%; found; 42.70%. Distills at 100°C between 2 and 4 mm.

EXAMPLE 3.
3-trimethylsilyl-5-methyl-2-oxazolidinone

Following example 1, but replacing the 2-oxazolidinone by 5-methyl-2-oxazolidinone (35.43 g; 0.35 mol) and operating in a similar way, the result is the crude product of the above heading, with a virtually quantitative yield. A light brown fluid liquid. Methanolysis in methylene chloride gives 5-methyl-2-oxazolidinone. Calculated: 58.37%; found 58.25%.

EXAMPLE 4. 5-phenyl-3-triethylsilyl-2-oxazolidinone

This example is performed in a similar way to example 1, with the 2-oxazolidinone and the trimethylchlorosilane being replaced by 5-phenyl-2-oxazolidinone (57.11 g; 0.35 mol) and triethylchlorosilane (63.3 g; 0.42 mol) respectively. Once the solvent has been evaporated off, the result is crude 5-phenyl-3-triethylsilyl-2-oxazolidinone with a virtually quantitative yield. By methanolysis 5-phenyl-2-oxazolidinone is obtained. Calculated: 69.33%; found: 69.05%.

EXAMPLE 5. 6(D(−)α-azido-phenylacetamido) penicillanic acid

A. 3-trimethylsilyl-2-oxazolidinone, (TMSO), I.

Stir and cool in an ice water bath a solution of 2-oxazolidinone (52.20 g; 0.6 mol) in 1,2-dichlorethane (650 ml). Then first add trimethylchlorosilane (107.0 ml; 0.8 mol) and then a further solution of triethylamine (105.0 ml; 0.75 mol) in 1,2-dichlorethane (100 ml). The reaction is moderately exothermic and the temperature is controlled to 25° to 30°C. Stir well for 60 minutes and maintain the operation protected from the ambient humidity. Thereafter the triethylamine hydrochloride precipitate is filtered and the solvent is evaporated from the filtrate at reduced pressure and at 40°C. Add ethyl acetate to the concentrate and then filter to separate residues of the base hydrochloride. Finally, the solvent is eliminated to give 98.30 g of a golden yellow liquid with a practically quantitative yield.

Distillation at reduced pressure gives 95 g of trimethylsilyl-2-oxazolidinone, a colorless liquid with d = 1.03 (18°) and bp = 97° at 3.5 mm. Insoluble in water and n-heptane, soluble in the majority of usual solvents.

Triethylamine hydrochloride (93.0 g) is isolated with a practically quantitative yield. Treatment with sodium hydroxide enables the organic base to be recovered integrally and it is recycled into the process.

B. Trimethylsilyl ester of 6-APA, II.

6-APA (42.80 g; 0.2 mol) is suspended in methylene chloride (500 ml) and TMSO (41.2 ml; 0.26 mol), quinoline (23.5 ml; 0.2 mol) and triethylamine (10 ml) are added with vigorous stirring. The mixture is protected from ambient humidity and the temperature is controlled to 35°C. The result is a practically colorless solution after 15 minutes. Stirring is continued until the temperature reaches 20°C.

C. Trimethylsilyl ester of 6(D(−)α-azido-phenylacetamido) penicillanic acid, III A mixture of D(−)α-azidophenylacetic acid (0.2 mol) activated with CSDF (0.2 mol) in methylene chloride, according to the method described in the literature (A.L. Palomo, "Afinidad", No. 284, 151, 1971), is added slowly over a period of 30 mins to solution 5B chilled to −15°C, to which quinoline (23.5 ml) had previously been added. The mixture is then stirred for 120 mins at 0°C to give a solution of III.

D. 6-(D(−)α-azidophenylacetamido) penicillanic acid, IV 150 ml of water are poured with stirring into the above solution, which is turbid with the hydrochloride of the tertiary base, the pH is adjusted to from 2.1 to 2.4 with hydrochloric acid and the organic phase is decanted off. After washing with water and drying with anhydrous sodium sulphate, a solution of the compound given in the heading is obtained. Thereafter there is added a solution of sodium 2-ethylhexanoate in methyl isobutyl ketone (90 ml, 47%), the mixture is diluted with n-heptane. Immediately the sodium salt of IV precipitates and is isolated by filtration to give the pure product (75 g, 98%), confirmed by IR spectrum, optical activity and bio test (990 µg/mg).

EXAMPLE 6. 7(D(−)α-azido-phenylacetamido) desacetoxycephalosporanic acid

A. 3-trimethylsilyl-2-oxazolidinone, (TMSO), I.

A solution of trimethylchlorosilane (214.0 ml; 1.6 mol) in 1,2-dimethoxyethane (200 ml) is added to a solution of 2-oxazolidinone (104.40 g; 1.2 mol) and trietylamine (210 ml; 1.5 mol) in 1,2-dimethoxyethane, stirred and chilled in an ice-water bath. The mixture is then vigorously stirred for 60 minutes, protected from the ambient humidity. After removing the base hydrochloride (185.0 g) by filtration, the solvent is evaporated off at reduced pressure to give 196.5 of I, whicn is distilled under vacuum to give a practically colorless liquid.

B. Trimethylsilyl ester of 7-ADCA, II

7-ADCA (42.80 g; 0.2 mol) is suspended in methylene chloride (500 ml), quinoline (46.0 ml; 0.4 mol), TMSO (41.2 ml; 0.26 mol) and triethylamine (10 ml) are added. The operation is performed in a dry atmosphere and the temperature is controlled to 35°C. Thorough stirring is maintained and a solution is prepared in 30 minutes. According to the purity and crystalline state of the 7-ADCA, if the reaction is held at ambient temperature, a solution is achieved after between 60 and 120 minutes.

C. Trimethylsilyl ester of 7(D(−)α-azidophenylacetamido) desacetoxycephalosporanic acid, III A mixture of D(−) α-azidophenylacetic acid, activated as in example 5C, is added slowly over a period of 30 mins to solution 6B at 0°C. The mixture is then stirred for 120 mins at ambient temperature to give a solution of III.

D. 7(D(−)α-azidophenylacetamido) desacetoxycephalosporanic acid, IV.

The above solution is treated in a similar way to Example 5D and gives 75 g of sodium salt (98%) confirmed by IR spectrum (beta-lactam nucleus and azido function) and bio test (993 µg/mg)

EXAMPLE 7. 7(D(−)α-amino-phenylacetamid) desacetoxycephalosporanic acid

A. 3-trimethylsilyl-2-oxazolidinone, (TMSO), I.

Prepare a solution of 2-oxazolidinone according to the amounts expressed in example 5A and add thereto first triethylamine and then trimethylchlorosilane diluted in 1,2-dichlorethane. Continue as described in example 5A to isolate by distillation at reduced pressure 95.2 g of I.

B. Trimethylsilyl ester of 7-ADCA, II

A suspension of 7-ADCA (21.4 g; 0.1 mol) in methylene chloride (150 ml), triethylamine (5 ml) and TMSO (25 ml) is stirred at ambient temperature, protected from humidity, to give a solution of II. If a larger amount of triethylamine is used, the preparation time of the solution is shortened.

C. Derivative of the trimethylsilyl ester of 7(D(—)α-amino-phenylacetamido) desacetoxycephalosporanic acid, III.

The previous solution is poured slowly over a mixed anhydride solution prepared in methylene chloride with the potassium salt of N(1-methyl-2 -ethoxyvinyl)D(—)α-a-minophenyl acetic acid (37.24 g; 0.12 mol) and ethyl chloroformate (11.75 g; 0.12 mol) at 0°C. The mixture is then stirred for 90 mins to give a solution of III.

D. 7(D(—)α-amino-phenylacetamido) desacetoxycephalosporanic acid, IV.

To the above solution there is added 150 ml of water and hydrochloric acid to a stable pH of 1.5–2.0. The water phase is decanted off, the pH is adjusted to 4.2 by way of a sodium hydroxide solution and the product is separated by filtration, washed with acetone and dried to give 30.4 g (83%) of the compound of the title; confirmed by IR spectrum, iodometrically determined purity (990 μg/mg) and optical activity.

$[\alpha]_D^{20} = + 143.7°$ (c = 1,0%, ClH 0,5N).

EXAMPLE 8.
6(3,0-chlorophenyl,5-methyl-4-isoxazolylcarboxamide) penicillanic acid A. 3-trimethylsilyl-2-oxazolidinone, (TMSO), I.

Oxazolidinone (52.20 g; 0.6 mol) is dissolved in 1,2-dimethoxyethane (300 ml) and after dilution with ethyl acetate (500 ml) there is first added trimethylchlorosilane (107.0 ml; 0.8 mol) and, thereafter, N-ethylpiperidine (79.2 g; 0.7 mol) with good stirring and temperature control to 30° by cooling. After 60 mins, the base hydrochloride is filtered and the ethyl acetate is distilled at reduced pressure to give 395 g of solution of I. Distillation of the solvent gives 97.65 g of silylating agent (TMSO).

B. Trimethylsilyl ester of 6-APA, II.

6-APA (42.80 g; 0.2 mol) is suspended in the solution of I in 1,2-dimethoxyethane (200 g, 24%) with good stirring. Triethylamine (10 ml) is added. After 60 mins at ambient temperature, the result is a solution of II.

C. Trimethylsilyl ester of 6 (3,0-chlorophenyl,5-methyl-4-isoxazolycarboxamido) penicillanic acid, III.

A further solution of 3(2-0-chlorophenyl)-5-methyl-4-isoxazolylcarboxylic acid (0.2 mol) activated according to the method described in the literature (A.L. Palomo and E. Torrens, "Afinidad" No. 290, page 993, 1971) and triethylamine to remove the hydrochloric acid is added slowly to the foregoing solution. The pH is controlled to 5 to 6 and after 60 mins stirring a 0°C, the result is a solution of III, turbid as a result of the precipitated hydrochloride.

D. 6(3,0-chlorophenyl-5-methyl-4-isoxazolylcarboxamido) penicillanic acid, IV.

Methylisobutyl ketone (250 ml) is added to the above preparation, the precipitate is separated by filtration and is washed with water (10 ml). After stirring for 15 mins, there is added a 45% solution of sodium 2-ethylhexanoate in n-butanol and the mixture is allowed to stand for 120 mins. The sodium salt is filtered and washed with n-heptane to give the compound of the title (93.9 g) with a yield of 98.7%. Confirmed by IR spectrum and iodometric evaluation (953 μg/mg).

In a similar way, the sodium salt of 3(2,6-dichlorophenyl-5-methyl-4-isoxazolylcarboxyamido) penicillanic acid is prepared.

EXAMPLE 9. 6(2,6-dimethoxybenzamido) penicillanic acid

A. 3-chlorodimethylsilyl-2-oxazolidinone, (CMSO), I.

To a solution of 2-oxazolidinone (104.40 g; 1.2 mol) in 1,2-dimethoxyethane (500 ml) diluted with ethyl acetate (500 ml), stirred and chilled in a cooling bath, there is added a further solution of dichlorodimethylsilane (156.7 ml; 1.3 mol) in ethyl acetate (500 ml) and thereafter tributylamine (222.4 g; 1.2 mol) whilst the temperature is controlled to 0°C. After stirring for 30 min, the tributylamine hydrochloride is filtered and the most volatile solvent is evaporated off at reduced pressure. The resulting liquid is diluted with n-heptane (2000 ml) and after standing for 15 mins, the lower phase is decanted off to give 215.0 g of I, in the form of a yellowish liquid with a practically quantitative yield. Distillation at reduced pressure gives an almost colorless liquid.

B. Chlorodimethylsilyl ester of 6-APA, II

Operating as in Example 5B, but replacing the TMSO by the silylating agent CMSO prepared above, a solution of II is obtained.

C. Chlorodimethylsilyl ester of 6(2,6-dimethoxybenzamido penicillanic acid.

2,6-dimethoxybenzoic acid is activated in a similar way to that described in Example 5C and as presented in that example, is added to a solution of the ester prepared as per 9B, to give a colorless solution of III.

D. 6(2,6-dimethoxybenzamido) penicillanic acid, IV.

Operating as in 5B, the sodium salt is obtained of the compound of the title, with a similar yield. Confirmed by IR spectrum and iodometric evaluation.

EXAMPLE 10. 6 (C(—)α-amino-p-hydroxyphenylacetamido) penicillanic acid

A. 3-trimethylsilyl-2-oxazolidinone, (TMSO), I.

Prepared as per example 5A but replacing the triethylamine by the equivalent amount of quinoline. The result is compound I.

B. Trimethylsilyl ester of 6-APA, II.

Using the above agent and operating in a similar way to example 5B, the result is a solution of II.

C. Derivative of the trimethylsilyl ester of 6 (D(—)α-amino-p-hydroxyphenylacetamido) penicillanic acid.

The above solution is added to a further solution of mixed anhydride prepared with D(—)α-amino-hydroxyphenyl acetic acid, ethyl acetylacetate and pivaloyl chloride following a method similar to the one described in the literature (E. Dane and T. Dockner, Ber. 98, 789, 1965) and following the procedure given in example 7C, the result is a solution of compound III.

D. 6 (D(—)α-amino-p-hydroxyphenylacetamido) penicillanic acid, IV.

In a similar way to the one described in example 7D, the compound of the title is isolated, confirmed by IR spectrum, iodometric evaluation and bio test (975 μg/mg).

If the same process is followed with D,Lα-amino-p-hydroxyphenylacetic acid, the result is the mixture of the epimer of the compound of the title.

EXAMPLE 11. 7(α-hexamin-phenylacetamido) desacetoxycephalosporanic acid

A. 3-trimethylsilyl-2-oxazolidinone, (TMSO), I.

Operating in the same way as in Example 8A, but replacing the n-ethylpiperidine with the equivalent amount of tripropylamine and then continuing as in Example 1 gives an identical yield of compound I.

B. Trimethylsilyl ester of 7-ADCA, II.

Operating as described in Example 6B and using the above silylating agent, a solution of II is obtained.

C. Trimethylsilyl ester of 7(α-hexamin-phenylacetamido) desacetoxycephalosporanic acid.

α-hexamin (urotropine) phenylacetic acid was prepared by the substitution of α-chlorophenylacetic acid by its silyl ester prepared from the acid and TMSO in the presence of triethylamine and treatment with urotropine, the ester then being split by isopropanol.

α-hexaminphenylacetic acid (31.07 g; 0.1 mol) is added to methylene chloride (300 ml) and cooled to 0°C. Under stirring dimethylformiminium N,chloride-chlorosulphite (0.1 mol) is slowly added. After standing for 120 mins, this mixture is slowly poured over a solution of II, prepared from 21.4 g of 7-ADCA, at a temperature of 0°C and in a similar way to example 6C, to give a solution of III.

D. 7(α-hexamin-phenylacetamido) desacetoxycephalosporanic acid

The solution obtained in C) above is filtered and there is then added isopropanol (100 ml). The solution is stirred for 30 mins at 0°C. The precipitate, washed with n-heptane and dried at low temperature, gives the compound of the title (45 g; 90%), confirmed by IR spectrum and iodometric evaluation.

Operating as in example 5D, and adding hydrochloric acid to a stable pH of from 1.5 to 2.0, the aqueous solution is decanted off, the pH is adjusted to 4.2 and 7(α-amino-phenylacetamido) desacetoxycephalosporanic acid (29.2 g; 82%) precipitates.

In a similar way and using the enanthiomers of α-chlorophenylacetic acid, the epimers are obtained after washing either with methanol and acid, or with water and acid of the compound of example 11D.

EXAMPLE 12. 6(benzamido) penicillanic acid

E. 3-benzoyl-2-oxazolidinone, VI

To a solution of 2-oxazolidinone (4.68 g; 0.05 mol) in 1,2-dichlorethane (60 ml), there is added benzoyl chloride (5.6 ml, 0.05 mol) and triethylamine (7.0 ml; 0.05 mol), with stirring at ambient temperature for 30 mins. The solution is then concentrated at reduced pressure and ethyl acetate is added, thereafter it is filtered to remove the base hydrochloride; the filtrate is partly evaporated and diluted with n-heptane and the precipitated solid is removed by filtration. After washing with water and drying, it gives 3-benzoyl-2-oxazolidinone (5.94 g; 90%). From absolute ethanol it crystallizes in nacar scales with m.p. = 166°–170°C. A portion of the substance in ethanol, with a catalytic amount of sodium ethoxide at room temperature immediately gives ethyl benzoate and, with aniline, benzanilide.

C. Trimethylsilyl ester of 6(benzamido) penicillanic acid, III

A solution of trimethylsilyl ester of 6-APA is prepared according to example 5B (1/8th solution) and 3-benzoyl-2-oxazolidinone (3.3 g; 0.025 mol) is added with stirring at ambient temperature for 30 mins. A solution of III is obtained.

D. 6(benzamido) penicillanic acid, IV

The above solution is mixed with water and stirred, the pH is adjusted to 2.0 with hydrochloric acid. The organic phase is decanted off and after being dried with anhydrous sodium sulphate, there is added thereto sodium 2-ethyl-hexanoate, the mixture is diluted with n-heptane (250 ml) and the sodium salt of IV precipitates. Was confirmed by IR spectrum and iodometric evaluation (988 μg/mg) giving 8.07 g with a yield of 95%.

EXAMPLE 13 7(p-methoxy-benzamido) desacetoxycephalosporanic acid

E. 3-(p-methoxybenzoyl)-2-oxazolidinone, VI.

p-methoxybenzoyl chloride (8.53 g; 0.05 mol) is added to a solution of 2-oxazolidinone (4.35 g; 0.05 mol) in 1,2-dimethoxyethane (35 ml), the solution is chilled to 0°C and beta-picoline (4 ml) and n-ethylpiperidine (5.66 g) are added. After stirring the mixture for 60 mins at the same temperature, it is diluted in n-heptane (250 ml) and the precipitate is removed by filtration; the solid, washed in water and dried gives 10.50 g(95%). Crystallized from ethanol, m.p. = 152°–4°C.

C. Trimethylsilyl ester of 7(p-methoxy-benzamido) desacetoxycephalosporanic acid, III.

To a solution of trimethylsilyl ester of 7-ADCA in methylene chloride (containing 0.025 mol) there is added compound 13E (0.025 mol) and the solution is stirred for 60 mins at a temperature of 30°C to give a solution of III.

D. 7(p-methoxybenzamido) desacetoxycephalosporanic acid, IV.

The above solution is treated in a similar way to Example 7D and gives the sodium salt of the compound of the title. Confirmed by IR spectrum.

EXAMPLE 14. 7(p-chloro-benzamido) cephalosporanic acid

E. 3-(p-chlorobenzoyl)-2-oxazolidinone, VI.

Operating as in Example 13E, but replacing the 1,2-dimethoxyethane by methylene chloride, the p-methoxybenzoyl chloride by p-chlorobenzoyl chloride (8.75 g; 0.05 mol) and the beta-picoline by quinoline, compound 14E is given (10.5 g; 93.6%). Crystallized from ethanol, m.p. = 162°–5°C.

C. Trimethylsilyl ester of 7(p-chloro-benzamido) cephalosporanic acid, III.

To a solution of trimethylsilyl ester of 7-ACA in methylene chloride (containing 0.025 mol) there is added compound 14E (0.025 mol) and the mixture is stirred for 60 mins at a temperature of 20°C to give a solution of III.

D. 7(p-chlorobenzamide) cephalosporanic acid, IV.

The above solution 14C is treated in a similar way to that of Example 5D and gives the sodium salt of the compound of the title. Confirmed by IR spectrum.

EXAMPLE 15. 6(p-nitro-benzamido) penicillanic acid.

E. 3-(p-nitrobenzoyl-2-oxazolidinone, VI.

Operating as per Example 13E, but replacing the p-methoxybenzoyl chloride by p-nitrobenzoyl chloride (9.27 g; 0.05 mol), compound 15E is given (10.71 g; 90.3%). Crystallized from ethanol, m.p. = 233°–5°C.

C. Trimethylsilyl ester of 6(p-nitrobenzamido) penicillanic acid, III.

Compound 15E (0.025 mol) is added to a solution of trimethylsilyl ester of 6-APA (containing 0.025 mol) and the solution is stirred for 120 mins at ambient temperature to give a solution of III.

D. 6-(p-nitrobenzamido) penicillanic acid, IV.

The above solution 15C is treated in a similar way to Example 5D and gives the sodium salt of the compound of the title. Confirmed by IR spectrum and iodometric evaluation.

What I claim is:
1. A 3-alkylsilyl-2-oxazolidinone of the formula

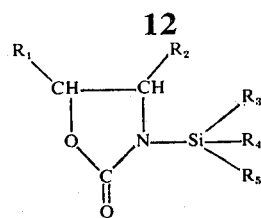

where $R_1$ and $R_2$ are each selected from the group consisting of hydrogen, phenyl, and alkyl having one to three carbon atoms, $R_3$ and $R_4$ are each alkyl having one to three carbon atoms and $R_5$ is an element selected from the group consisting of alkyl having one to three carbon atoms and chlorine.

2. 3-trimethylsilyl-2-oxazolidinone.
3. 3-triethylsilyl-2-oxazolidinone.
4. 3-trimethylsilyl-5-methyl-2-oxazolidinone.
5. 5-phenyl-3-triethylsilyl-2-oxazolidinone.

* * * * *